US008592360B2

(12) United States Patent  (10) Patent No.: US 8,592,360 B2
Muratore et al.  (45) Date of Patent: Nov. 26, 2013

(54) ALDEHYDES AND NITRILES FROM ISOPHORONE AND THE USE THEREOF IN PERFUMERY

(75) Inventors: Agnés Muratore, Valbonne (FR); Jean-Jacques Chanot, Speracedes (FR)

(73) Assignee: V. Mane Fils, Bar sur Loup (FR)

( * ) Notice: Subject to any disclaimer, the term of this patent is extended or adjusted under 35 U.S.C. 154(b) by 0 days.

(21) Appl. No.: 13/496,783

(22) PCT Filed: Sep. 17, 2010

(86) PCT No.: PCT/IB2010/054213
§ 371 (c)(1),
(2), (4) Date: Jun. 6, 2012

(87) PCT Pub. No.: WO2011/033479
PCT Pub. Date: Mar. 24, 2011

(65) Prior Publication Data
US 2012/0238486 A1  Sep. 20, 2012

(30) Foreign Application Priority Data
Sep. 18, 2009  (FR) ...................................... 09 56422

(51) Int. Cl.
*A61Q 13/00* (2006.01)
(52) U.S. Cl.
USPC ............................................................ 512/6
(58) Field of Classification Search
USPC ............................................ 512/6; 558/432
See application file for complete search history.

(56) References Cited

U.S. PATENT DOCUMENTS

| 4,477,683 A | * | 10/1984 | Virgilio et al. | ................ 568/379 |
| 4,912,088 A | * | 3/1990 | Brunke et al. | .................... 512/6 |
| 5,073,538 A | | 12/1991 | Heullmann et al. | |

FOREIGN PATENT DOCUMENTS

EP  0146 859  7/1985

OTHER PUBLICATIONS

English Translation of Written Opinion for PCT/IB2010/054213.
Wheeler et al, "Dissociation Constants of the Cyanohydrins of Some Methyl-Substituted Cyclobutanones, Cyclopentanones, and Cycloheptanones. Conformation of These Rings", Mar. 1964, pp. 718-721, vol. 29.
Bruns et al, "Syntheses with 2,2,4-/2,4,4-Trimethylcyclopentanone" Nov. 16-20, 1986, pp. 767-776, Proceedings of the 10$^{th}$ International Congress of Essential Oils, Fragrances and Flavors, Washington, D.C.
International Search Report for PCT/IB2010/054213.

* cited by examiner

*Primary Examiner* — Ling Choi
*Assistant Examiner* — Lanee Reuther
(74) *Attorney, Agent, or Firm* — B. Aaron Schulman; Stites & Harbison PLLC

(57) ABSTRACT

The invention relates to novel aldehydes and nitriles from isophorone with general formula (I) having a specific fragrance (Formula I) (I), as well as to the use of said compounds in perfumery.

(I)

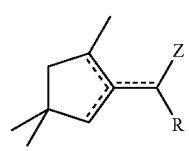

10 Claims, No Drawings

ALDEHYDES AND NITRILES FROM ISOPHORONE AND THE USE THEREOF IN PERFUMERY

The present invention relates to novel aldehydes and nitriles resulting from isophorone exhibiting a specific fragrance and to the use of these compounds in perfumery.

The term "perfumery" is used here to denote not only perfumery in the usual sense of the term but also the other fields in which the odor of products is important. Perfumery compositions in the usual sense of the term may be involved, such as fragrance bases, perfume concentrates, eaux de Cologne, toilet waters, fragrances and similar products; topical compositions, in particular cosmetics, such as creams for the face and body, talcum powders, hair oils, shampoos, hair lotions, bath salts and oils, shower and bath gels, toilet soaps, antiperspirants and deodorants for the body, shaving lotions and creams, soaps, creams, toothpastes, mouthwashes, pomades and similar products; and cleaning products, such as softeners, detergents, washing powders, air fresheners and similar products.

The terms "fragrance", "fragrant", and "odorous" are used here interchangeably for any organoleptic compound which pleasingly stimulates the sense of smell.

The term "to mask" or "masking" is understood to mean to reduce or eliminate the perception of an unpleasant odor or of an unpleasant taste generated by one or more molecules participating in the composition of a product.

Numerous derivatives of cyclopentane type, in particular compounds comprising a campholene backbone or cyclopentanones, are described in the literature for their advantageous olfactory properties. For example, patent applications U.S. Pat. No. 5,073,538, EP 0 146 859 and U.S. Pat. No. 4,477,683, and Bruns et al. (Bruns K and Weber U.; *Development in Food Science*, 1998, 18 (F&F), 767-776) describe 2,4,4-trimethyl-cyclopentane derivatives, some of which are of interest to the perfumery industry. However, very few compounds of nitrile or aldehyde type derived from 2,4,4-trimethyl-cyclopentane have been described in the literature (U.S. Pat. No. 3,931,143, U.S. Pat. No. 4,477,683 and Wheler O. H. and De Rodriguez E. G.; *J. Org. Chem.*, 1964, 29(3), 718-721) and none of these descriptions gives a report of their olfactory properties.

Generally, the perfumery industry has a constant need for novel odorous molecules in order to increase the range of notes offered to perfumers for their creations. Furthermore, this need is becoming increasingly great as the perfumery industry has had to face a hardening in international regulations, in addition to environmental awareness and an enhanced expectation of consumers. The object of the invention is thus to provide novel fragrances and/or odorous compounds.

The present invention relates to novel aldehydes and nitriles resulting from isophorone. These compounds have the advantage of being accessible by a reliable and inexpensive preparation.

A subject matter of the present invention is thus the compounds of general formula (I) below:

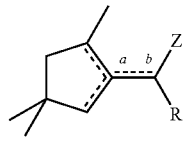

(I)

in which:
R is a hydrogen atom, a $C_1$-$C_6$ alkyl group, a $C_2$-$C_6$ alkenyl group or a =$CH_2$ group;
Z is a CN or CHO group; and
at most one of the bonds represented by dashes is present;
provided that:
if Z is a CHO group and one of the bonds represented by dashes is present, then R is not a hydrogen atom, and
if the bond represented by dashes between the carbons Ca and Cb is present, then R is not a =$CH_2$ group.

The term "$C_1$-$C_6$ alkyl" is understood to mean, within the meaning of the present invention, any monovalent radical derived from a saturated, linear or branched, carbon-based chain comprising from 1 to 6 carbon atoms, in particular the methyl, ethyl, n-propyl, isopropyl, n-butyl, isobutyl, tert-butyl, pentyl and hexyl groups. Preferred alkyl groups are the methyl, ethyl, n-propyl, isopropyl, n-butyl, isobutyl and n-pentyl groups.

The term "$C_2$-$C_6$ alkenyl" is understood to mean, within the meaning of the present invention, any monovalent radical derived from a linear or branched carbon-based chain comprising from 2 to 6 carbon atoms and comprising at least one double bond, in particular the ethenyl, n-propenyl, isopropenyl, n-butenyl, isobutenyl, tert-butenyl, n-pententyl and n-hexenyl groups. Preferred alkenyl groups are the ethenyl, n-propenyl, isopropenyl, n-butenyl, isobutenyl and n-pentenyl groups.

Another subject matter of the present invention is the stereoisomers of formula (I), in particular the diastereoisomers of formula (I), and the mixtures, in all proportions, of these isomers.

In particular, the present invention relates to the compounds of general formula (Ia):

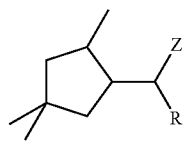

(Ia)

in which:
R is a hydrogen atom, a $C_1$-$C_6$ alkyl group, a $C_2$-$C_6$ alkenyl group or a =$CH_2$ group;
Z is a CN or CHO group;
the compounds of general formulae (Ib) and (Ic):

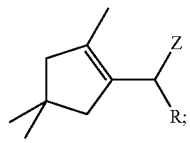

(Ib)

-continued

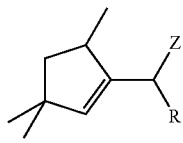
(Ic)

in which:
   R is a hydrogen atom, a $C_1$-$C_6$ alkyl group, a $C_2$-$C_6$ alkenyl group or a =$CH_2$ group;
   Z is a CN or CHO group; and
   provided that, if Z is a CHO group, then R is not a hydrogen atom;

those of formulae (Ib) and (Ic), and the compounds of general formula (Id):

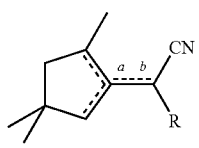
(Id)

in which:
   R is a hydrogen atom, a $C_1$-$C_6$ alkyl group or a $C_2$-$C_6$ alkenyl group;
   Z is a CN or CHO group; and
   provided that, if Z is a CHO group, then R is not a hydrogen atom.

In a first embodiment, the present invention relates to the compounds of general formula (I'):

(I')

in which:
   R is a hydrogen atom, a $C_1$-$C_6$ alkyl group, a $C_2$-$C_6$ alkenyl group or a =$CH_2$ group; preferably, R is a hydrogen atom, a $C_1$-$C_6$ alkyl group or a =$CH_2$ group; more preferably, R is a hydrogen atom or a methyl, ethyl, n-propyl, isopropyl or =$CH_2$ group; more preferably still, R is a hydrogen atom or a methyl or =$CH_2$ group; and
   at most one of the bonds represented by dashes is present;
   provided that, if the bond represented by dashes between the carbon Ca and Cb is present, then R is not a =$CH_2$ group.

Compounds of formula (I') which are particularly advantageous are the compounds (1) to (6) represented in table 1.

A first alternative form of this embodiment relates to the compounds of formula (Ia'):

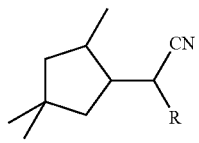
(Ia')

in which:
   R is a hydrogen atom, a $C_1$-$C_6$ alkyl group, a $C_2$-$C_6$ alkenyl group or a =$CH_2$ group; preferably, R is a hydrogen atom, a $C_1$-$C_6$ alkyl group or a =$CH_2$ group; more preferably, R is a hydrogen atom or a methyl, ethyl, n-propyl, isopropyl or =$CH_2$ group; more preferably still, R is a hydrogen atom or a methyl or =$CH_2$ group.

A second alternative form relates to the compounds of formula (Ib'):

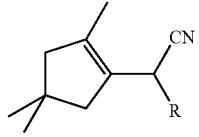
(Ib')

in which:
   R is a hydrogen atom, a $C_1$-$C_6$ alkyl group, a $C_2$-$C_6$ alkenyl group or a =$CH_2$ group; preferably, R is a hydrogen atom, a $C_1$-$C_6$ alkyl group or a =$CH_2$ group; more preferably, R is a hydrogen atom or a methyl, ethyl, n-propyl, isopropyl or =$CH_2$ group; more preferably still, R is a hydrogen atom or a methyl or =$CH_2$ group.

A third alternative form of this embodiment also relates to the compounds of formula (Ic'):

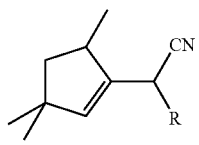
(Ic')

in which:
   R is a hydrogen atom, a $C_1$-$C_6$ alkyl group, a $C_2$-$C_6$ alkenyl group or a =$CH_2$ group; preferably, R is a hydrogen atom, a $C_1$-$C_6$ alkyl group or a =$CH_2$ group; more preferably, R is a hydrogen atom or a methyl, ethyl, n-propyl, isopropyl or =$CH_2$ group; more preferably still, R is a hydrogen atom or a methyl or =$CH_2$ group.

Finally, a final alternative form of this embodiment relates to the compounds of formula (Id'):

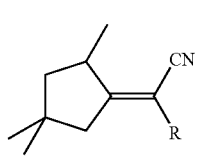
(Id')

in which:
   R is a hydrogen atom, a $C_1$-$C_6$ alkyl group or a $C_2$-$C_6$ alkenyl group; preferably, R is a hydrogen atom or a $C_1$-$C_6$ alkyl group; more preferably, R is a hydrogen atom or a methyl, ethyl, n-propyl or isopropyl group; more preferably still, R is a hydrogen atom or a methyl group.

In a second embodiment, the present invention is also targeted at the compounds of general formula (I″):

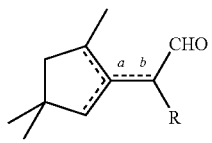

(I″)

in which:
R is a hydrogen atom, a $C_1$-$C_6$ alkyl group, a $C_2$-$C_6$ alkenyl group or a $=CH_2$ group; preferably, R is a hydrogen atom, a $C_1$-$C_6$ alkyl group or a $=CH_2$ group; more preferably, R is a hydrogen atom or a methyl, ethyl, n-propyl, isopropyl or $=CH_2$ group; more preferably still, R is a hydrogen atom or a methyl or $=CH_2$ group; and
at most one of the bonds represented by dashes is present; provided that, if one of the bonds represented by dashes is present, then R is not a hydrogen atom, and if the bond represented by dashes between the carbon Ca and Cb is present, then R is not a $=CH_2$ group.

Compounds of formula (I″) which are particularly advantageous are the compounds (7) to (9) represented in table 1.

A first alternative form of this embodiment relates to the compounds of formula (Ia″):

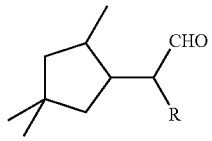

(Ia″)

in which:
R is a hydrogen atom, a $C_1$-$C_6$ alkyl group, a $C_2$-$C_6$ alkenyl group or a $=CH_2$ group; preferably, R is a hydrogen atom, a $C_1$-$C_6$ alkyl group or a $=CH_2$ group; more preferably, R is a hydrogen atom or a methyl, ethyl, n-propyl, isopropyl or $=CH_2$ group; more preferably still, R is a hydrogen atom or a methyl or $=CH_2$ group.

A second alternative form relates to the compounds of formula (Ib″):

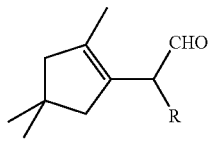

(Ib″)

in which:
R is a $C_1$-$C_6$ alkyl group, a $C_2$-$C_6$ alkenyl group or a $=CH_2$ group; preferably, R is a $C_1$-$C_6$ alkyl group or a $=CH_2$ group; more preferably, R is a methyl, ethyl, n-propyl, isopropyl or $=CH_2$ group; more preferably still, R is a methyl or $=CH_2$ group.

A third alternative form of this embodiment also relates to the compounds of formula (Ic″):

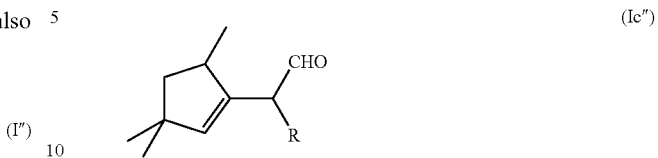

(Ic″)

in which:
R is a $C_1$-$C_6$ alkyl group, a $C_2$-$C_6$ alkenyl group or a $=CH_2$ group; preferably, R is a $C_1$-$C_6$ alkyl group or a $=CH_2$ group; more preferably, R is a methyl, ethyl, n-propyl, isopropyl or $=CH_2$ group; more preferably still, R is a methyl or $=CH_2$ group.

Finally, a final alternative form of this embodiment relates to the compounds of formula (Id″):

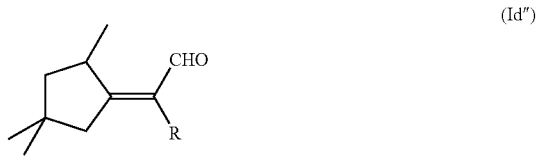

(Id″)

in which:
R is a $C_1$-$C_6$ alkyl group or a $C_2$-$C_6$ alkenyl group; preferably, R is a $C_1$-$C_6$ alkyl group; more preferably, R is a methyl, ethyl, n-propyl or isopropyl group; more preferably still, R is a methyl group.

More particularly, the invention relates to the compounds of formula (I) represented in table 1.

TABLE 1

| Compound | Formula | Compound | Formula |
|---|---|---|---|
| 1 | ![structure with CN] | 2 | ![structure with CN] |
| 3 | ![structure with CN] | 4 | ![structure with CN] |
| 5 | ![structure with CN] | 6 | ![structure with CN] |
| 7 | ![structure with CHO] | 8 | ![structure with CHO] |

TABLE 1-continued

| Compound | Formula | Compound | Formula |
|---|---|---|---|
| 9 | 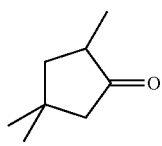 | | |

The invention comprises all the enantiomers and diastereoisomers of the compounds of formula (I), alone or as mixtures. The presence in the structure of the compounds of formula (I) of centers of asymmetry results in the existence, for each of them, of the enantiomeric forms. The invention comprises the compounds represented by the general formula (I) in the form of mixtures of enantiomers in variable proportions, in particular racemic mixtures. The invention also comprises the compounds of formula (I) in the form of just one enantiomer. The preparation of the mixtures of enantiomers or of pure forms is carried out by methods known to a person skilled in the art, for example by using optically enriched or optically pure starting materials.

The compounds of formula (I) have the advantage of being accessible by a reliable and inexpensive preparation. Thus, the compounds of formula (I) can be obtained from isophorone.

The present invention also relates to a process for the preparation of a compound of formula (I) comprising a stage consisting in reacting the compound of formula (A):

(A)

with a diethylphosphonoalkylacetonitrile of formula RCH(CN)PO(OC$_2$H$_5$)$_2$ in which R is a hydrogen atom, a C$_1$-C$_6$ alkyl group or a C$_2$-C$_6$ alkenyl group; preferably, R is a hydrogen atom or a C$_1$-C$_6$ alkyl group; more preferably, R is a hydrogen atom or a methyl, ethyl, n-propyl or isopropyl group; more preferably still, R is a hydrogen atom or a methyl group; or
with an alkyl cyanoacetate of formula NCCH$_2$COOR' in which R' is a C$_1$-C$_4$ alkyl group; preferably R' is a methyl group.

In a first step, isophorone epoxide is obtained from isophorone by a Weitz-Scheffer epoxidation. The rearrangement of the isophorone epoxide in an acidic medium results in 2,4,4-trimethylcyclopentanone (A).

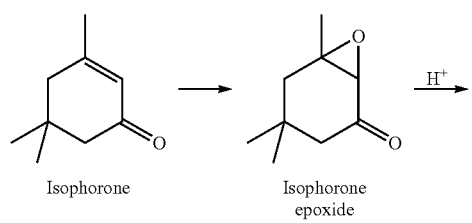

Isophorone → Isophorone epoxide →$^{H^+}$

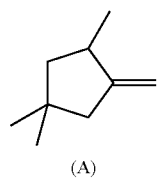

(A)

In a first embodiment, the compounds of formulae (Ia') and (Id') are obtained according to scheme 1:

Scheme 1

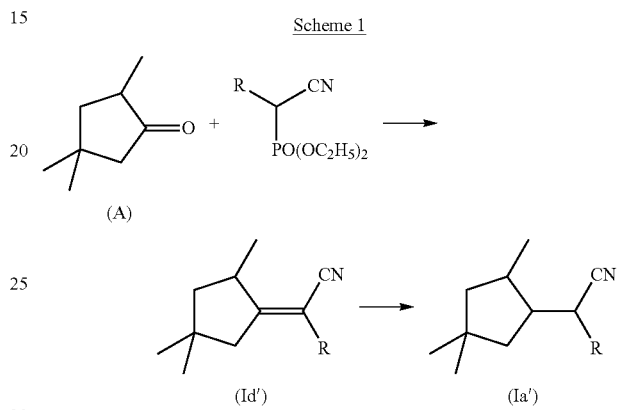

(Id')    (Ia')

The action of a diethylphosphonoalkylacetonitrile of formula RCH(CN)PO(OC$_2$H$_5$)$_2$, R being as defined above, on the cyclopentanone of formula (A) results in the compounds of formula (Id'). This reaction is advantageously carried out in the presence of a base, such as an organolithium base, preferably butyllithium (BuLi), in a nonpolar solvent, such as tetrahydrofuran. The hydrogenation of the compounds of formula (Id') makes it possible to obtain the compounds of formula (Ia') in which R cannot be =CH$_2$. The hydrogenation is carried out under conditions well known to a person skilled in the art, for example in an autoclave under a hydrogen atmosphere in the presence of a 5% palladium-on-charcoal catalyst.

In a second embodiment, the compounds of formulae (Ib') and (Ic') as well as the compounds (5) and (6) are obtained according to scheme 2:

Scheme 2

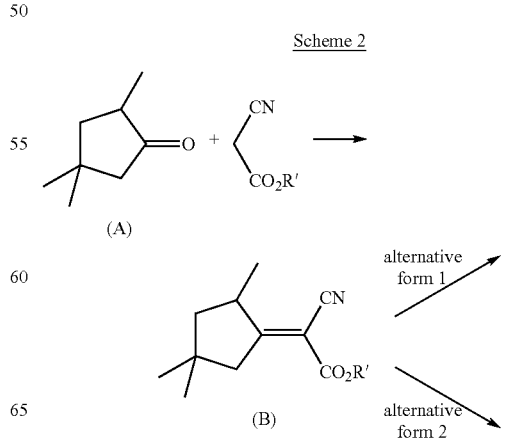

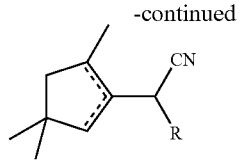

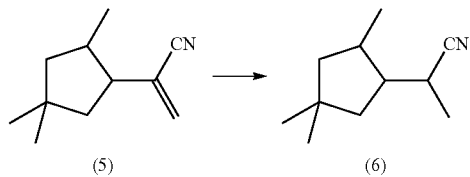

In a first step, the cyclopentanone of formula (A) is condensed with an alkyl cyanoacetate of formula NCCH$_2$COOR', in which R' is a C$_1$-C$_4$ alkyl group, preferably a methyl group, to give the compound of formula (B). The condensation is carried out, for example, in the presence of acetic acid (AcOH) and ammonium acetate (AcONH$_4$) in a nonpolar aprotic solvent, such as cyclohexane, at reflux temperature.

In a first alternative form, the compound (B) is subsequently subjected to a decarboxylation, optionally followed by a hydrogenation and/or by an alkylation, to result in the compounds of formula (Ia'), (Ib') or (Ic'). The decarboxylation is advantageously carried out in the presence of an alkali metal halide, such as lithium chloride, in a polar solvent, such as N-methylpyrrolidone. The hydrogenation is carried out under conditions well known to a person skilled in the art, for example in an autoclave under a hydrogen atmosphere in the presence of a 5% palladium-on-charcoal catalyst. The alkylation can be carried out using an alkylating agent, chosen from an alkyl bromide, an alkyl iodide or an alkyl chloride, and a base, such as, for example, lithium diisopropylamide or potassium tert-butoxide. An appropriate solvent for this reaction may be a nonpolar solvent, such as tetrahydrofuran, or a polar aprotic solvent, such as dimethylformamide.

In a second alternative form, the reduction of the compound of formula (B), followed by a dehydration and optionally by a hydrogenation, makes it possible to obtain the compounds (5) and (6). The reduction is advantageously carried out using a hydride, such as NaBH$_4$. The hydrogenation is carried out under conditions well known to a person skilled in the art, for example in an autoclave under a hydrogen atmosphere in the presence of a 5% palladium-on-charcoal catalyst.

Generally, the compounds of formula (I") are obtained by the controlled reduction of the nitrile functional group of the corresponding compounds of formula (I') to give the aldehyde functional group. This reduction can be carried out, for example, in the presence of diisobutylaluminum hydride (Dibal) in a nonpolar solvent such as toluene.

Due to their odorous properties, the compounds of formula (I) have a great variety of uses in perfumery, in particular and without implied limitation in cosmetics and for cleaning products.

Another subject matter of the invention is thus the use of at least one compound of formula (I) according to the invention as fragrant agent or compound, as odor-masking agent or as odor-neutralizing agent, alone or as a mixture with one or more other odorous compounds known to a person skilled in the art and which a person skilled in the art is in a position to choose according to the effect desired. The additional odorous agent or agents can be compounds of formula (I) or other odorous agents known to a person skilled in the art.

For the same reasons, the invention also relates to a method for scenting a base product comprising the addition of a compound of the invention to said base product. The compound of the invention can be added alone or as a mixture with one or more other odorous compounds known to a person skilled in the art and which a person skilled in the art is in a position to choose according to the effect desired. The additional odorous agent or agents can be compounds of formula (I) or other odorous agents known to a person skilled in the art. Said base product can in particular be a perfumery composition, in particular a fragrance base or a perfume concentrate, an eaux de Cologne, a toilet water or a fragrance; a cosmetic composition, in particular cream for the face and body, talcum powder, oil for the hair or for the body, shampoo, hair lotion, bath salt, bath oil, shower gel, bath gel, toilet soap, antiperspirant for the body, deodorant for the body, shaving lotion or cream, shaving soaps, cream, toothpaste, mouthwash or pomade; or a cleaning product, in particular softener, detergent, washing powder or air freshener.

Another subject matter of the invention is the compositions comprising a base product and an effective amount of one or more compounds of formula (I) according to the invention.

It can be a composition which is itself odorous or a composition in which the odorous agent is used to mask or neutralize certain odors.

The base product will be easily determined by a person skilled in the art according to the composition envisaged and thus the use envisaged, the usual components for which, such as solvent(s) and/or adjuvant(s), are well known.

The effective amount of the compounds of formula (I) according to the invention incorporated in the composition will vary according to the nature of the composition, the odorous effect desired and the nature of the other odorous or nonodorous compounds possibly present and can be easily determined by a person skilled in the art, it being known that it can vary within a very broad range from 0.1 to 99% by weight, in particular 0.1 to 50% by weight, especially 0.1 to 30% by weight.

The compounds of formula (I) according to the invention can be used as is or they can be incorporated in or on an inert support material or a support material which can comprise other active ingredients of the finished composition. A great variety of support materials can be employed, including, for example, polar solvents, oils, fats, finely divided solids, cyclodextrins, maltodextrins, gums, resins and any other support material known for such compositions.

Another subject matter of the invention is thus the use of the compounds of formula (I) in the preparation of an odorous composition or of an odorous article in the applications described above, in particular in perfumery, in cosmetics, for example for shampoos or soaps, and in cleaning products, such as softeners or washing powders.

The invention relates in particular to a perfumery composition, especially a fragrance base or a perfume concentrate, an eau de Cologne, a toilet water or a fragrance, comprising at least one compound of formula (I) or a composition comprising at least one compound of formula (I).

The invention also relates in particular to a cosmetic composition, in particular a cream for the face and body, talcum powder, oil for the hair or for the body, shampoo, hair lotion, bath salt, bath oil, shower gel, bath gel, toilet soap, antiperspirant for the body, deodorant for the body, shaving lotion or cream, shaving soap, cream, toothpaste, mouthwash or pomade, comprising at least one compound of formula (I) or at least one composition comprising at least one compound of formula (I). Another subject matter of the invention is a preventative or nonpreventative cosmetic treatment or care method employing at least one compound of formula (I) or at least one composition comprising at least one compound of formula (I).

The invention also relates to a cleaning product, in particular softener, detergent, washing powder or air freshener, comprising at least one compound of formula (I) or at least one composition comprising at least one compound of formula (I).

The compounds according to the invention can be used, alone or in combination, as is or can be incorporated in or on an inert support material or a support material which can comprise other active ingredients of the finished composition. A great variety of support materials can be employed, including, for example, polar solvents, oils, fats, finely divided solids, cyclodextrins, maltodextrins, gums, resins and any other support materials known for such compositions.

The following examples further illustrate the various processes for the manufacture of the novel compounds according to the invention, and also their use and their advantage. These examples are presented only with an illustrative purpose and may not be regarded as limitations of the invention.

EXAMPLE 1

Preparation of 2-(2,4,4-trimethylcyclopent-1-enyl) acetonitrile (1) and 2-(3,3,5-trimethylcyclopent-1-enyl) acetonitrile (2)

The cyclopentanone A, 1.5 eq. of methyl cyanoacetate, 1 eq. of acetic acid and 10 mol % of ammonium acetate are placed in cyclohexane in the round-bottomed flask. The reaction medium is brought to reflux in order to remove the water formed using a apparatus of Dean-Stark type. After refluxing overnight, the conversion of A is satisfactory (>90%) and the reaction medium is thus allowed to return to ambient temperature. Washing is carried out with a sodium bicarbonate solution and then with an aqueous sodium chloride solution. After drying over magnesium sulfate, filtering through paper and evaporating the solvent, the crude product B is distilled under reduced pressure.

B.p.=80° C./0.3 torr

The methyl 2-cyano-2-(2,4,4-trimethylcyclopentylidene) acetate B is placed in a round-bottomed flask with 2 eq. of lithium chloride in a 98:2 mixture of NMP (N-methylpyrrolidone) and water. The mixture is stirred at 150° C. After 3 hours, the reaction medium is cooled to ambient temperature before being poured onto a 1% HCl solution. Stirring is carried out for a few minutes and then extraction is carried out twice with MTBE (methyl tert-butyl ether). The combined organic phases are washed with a sodium bicarbonate solution and then with an aqueous sodium chloride solution. After drying over magnesium sulfate, filtering through paper and evaporating the solvent, the crude product is distilled under reduced pressure. A 70:30 mixture of 2-(2,4,4-trimethylcyclopent-1-enyl)acetonitrile and 2-(3,3,5-trimethylcyclopent-1-enyl)-acetonitrile is obtained.

B.p.=78-82° C./6 torr

Olfactory description: spicy, cumin, woody, citrus, powerful.

Major Isomer:

$^1$H NMR (200 MHz, CDCl$_3$): δ (ppm) 1.08 (s, 6H), 1.63 (s, 3H), 2.15 (s, 2H), 2.25 (s, 2H), 3.08 (s, 2H).

$^{13}$C NMR (50 MHz, CDCl$_3$): δ (ppm) 17.43, 19.82, 30.07, 30.19, 50.99, 53.84, 121.95, 136.53, 136.54.

MS [e/m (%)]: 149 (M$^+$, 45), 135 (10), 134 (100), 109 (43), 108 (15), 107 (27), 94 (21), 93 (66), 91 (26), 79 (22), 77 (18), 67 (16), 41 (14), 39 (13).

Minor Isomer:

$^1$H NMR (200 MHz, CDCl$_3$): δ (ppm) 1.02-1.04 (m, 3H), 1.08 (s, 6H), 1.10-1.20 (m, 2H), 1.95-2.05 (m, 1H), 3.01 (s, 2H), 5.56 (s, 1H).

$^{13}$C NMR (50 MHz, CDCl$_3$): δ (ppm) 14.40, 18.22, 28.52, 36.70, 40.77, 48.92, 118.08, 134.15, 139.95

MS [e/m (%)]: 149 (M$^+$, 53), 148 (22), 135 (11), 134 (94), 122 (10), 120 (12), 109 (26), 108 (35), 107 (48), 106 (22), (38), 93 (48), 92 (15), 91 (27), 83 (100), 80 (19), 79 (27), 77 (23), 69 (37), 67 (21), 66 (30), 65 (22), 56 (20), (33), 54 (10), 53 (15), 51 (11), 43 (10), 41 (41), 39 (31).

IR (film, cm$^{-1}$): 759w, 840w, 931w, 1070w, 1159w, 1241w, 1315w, 1364w, 1415m, 1446m, 2249m, 2837m, 2866m, 2954s.

EXAMPLE 2

Preparation of 2-(2,4,4-trimethylcyclo-pentylidene)acetonitrile (3)

1.1 eq. of diethylphosphonoacetonitrile are placed in THF (tetrahydrofuran) under an inert atmosphere. 1.1 eq. of a solution of butyllithium in hexane are added thereto dropwise at approximately 10° C. The mixture is subsequently stirred at ambient temperature for one hour before adding, dropwise, 1 eq. of cyclopentanone A at approximately 10° C. The reaction medium is stirred at ambient temperature for a few hours and is then poured onto a 10% HCl solution. The aqueous phase is extracted three times with MTBE. The combined organic phases are washed with a sodium bicarbonate solution and then with an aqueous sodium chloride solution. After drying over magnesium sulfate, filtering through paper and evaporating the solvent, the crude product is distilled under reduced pressure. A 75:25 mixture of the trans and cis isomers of 2-(2,4,4-trimethyl-cyclopentylidene) acetonitrile is obtained.

B.p.=85° C./6 torr

Olfactory description: fresh, citrus, citrus fruit, green, powerful.

Major Isomer:

$^1$H NMR (200 MHz, CDCl$_3$): δ (ppm) 0.99 (s, 3H), 1.12 (s, 6H), 1.20-1.32 (m, 2H), 1.72-1.95 (m, 1H), 2.23-2.61 (m, 1H), 2.76-2.82 (m, 1H), 5.12 (s, 1H).

$^{13}$C NMR (50 MHz, CDCl$_3$): δ (ppm) 18.88, 28.01, 29.37, 37.84, 39.22, 48.59, 49.41, 91.17, 117.93, 178.84.

MS [e/m (%)]: 149 (M$^+$, 47), 148 (21), 135 (11), 134 (90), 122 (11), 120 (12), 109 (22), 108 (34), 107 (42), 106 (18), (10), 94 (35), 93 (49), 92 (15), 91 (22), 84 (10), 83 (100), 81 (15), 80 (19), 79 (26), 78 (10), 77 (20), 69 (33), 67 (19), 66 (29), 65 (21), 56 (22), 55 (35), 53 (15), 51 (11), 43 (10), 41 (40), 39 (30).

Minor Isomer:

$^1$H NMR (200 MHz, CDCl$_3$): δ (ppm) 0.89 (s, 3H), 1.14 (s, 6H), 1.20-1.32 (m, 2H), 1.72-1.95 (m, 1H), 2.23-2.61 (m, 1H), 2.76-2.82 (m, 1H), 5.24 (s, 1H).

$^{13}$C NMR (50 MHz, CDCl$_3$): δ (ppm) 19.93, 27.24, 28.88, 38.06, 38.58, 49.63, 50.18, 91.50, 117.93, 178.84.

MS [e/m (%)]: 149 (M$^+$, 12), 135 (10), 134 (100), 109 (17), 107 (11), 94 (20), 93 (82), 91 (21), 79 (20), 77 (14), 41 (12).

IR (film, cm$^{-1}$): 770w, 795w, 809s, 880w, 996w, 1268w, 1320w, 1369m, 1387m, 1420m, 1463s, 1637s, 2216s, 2870m, 2956s.

EXAMPLE 3

Preparation of
2-(2,4,4-trimethylcyclopentyl)-acetonitrile (4)

A solution containing 1 equivalent of a mixture of the compounds 1 and 2 obtained in example 1 in toluene and 5% by weight of 5% palladium-on-charcoal is placed in an autoclave, under 20 bar of hydrogen, at 40° C. At the end of the reaction, the autoclave is purged with nitrogen and the solution is filtered through celite. The filtrate is concentrated. The crude product, obtained in the form of two diastereomers in proportions of 70:30, is purified by distillation.

B.p.=80° C./6 torr
Olfactory description: green, fresh, zest, powerful.
Major Isomer:
$^1$H NMR (200 MHz, CDCl$_3$): δ (ppm) 0.92-1.08 (m, 3H), 1.04 (s, 6H), 1.15-1.42 (m, 2H), 1.60-1.87 (m, 3H), 2.23-2.44 (m, 3H).
$^{13}$C NMR (50 MHz, CDCl$_3$): δ (ppm) 18.82, 21.33, 31.54, 37.09, 39.94, 43.66, 47.86, 50.59, 119.42.
MS [e/m (%)]: 151 (M$^+$, 0.3), 136 (39), 119 (20), 111 (21), 108 (16), 96 (13), 95 (100), 83 (67), 82 (26), 69 (30), 67 (18), 56 (11), 55 (25), 41 (28), 39 (14).
Minor Isomer:
$^1$H NMR (200 MHz, CDCl$_3$): δ (ppm) 0.92-1.08 (m, 3H), 1.04 (s, 6H), 1.15-1.42 (m, 2H), 1.60-1.87 (m, 3H), 2.23-2.44 (m, 3H).
$^{13}$C NMR (50 MHz, CDCl$_3$): $^{13}$C NMR (50 MHz, CDCl$_3$): δ (ppm) 16.16, 19.29, 30.43, 35.47, 37.09, 39.04, 46.71, 49.42, 120.36.
$^1$H NMR (200 MHz, CDCl$_3$): (ppm) 0.92-1.08 (m, 3H), 1.04 (s, 6H), 1.15-1.42 (m, 2H), 1.60-1.87 (m, 3H), 2.23-2.44 (m, 3H).
$^{13}$C NMR (50 MHz, CDCl$_3$): (ppm) 18.82, 21.33, 31.54, 37.09, 39.94, 43.66, 47.86, 50.59, 119.42
MS [e/m (%)]: 151 (M$^+$, 0.3), 136 (39), 119 (20), 111 (21), 108 (16), 96 (13), 95 (100), 83 (67), 82 (26), 69 (30), 67 (18), 56 (11), 55 (25), 41 (28), 39 (14).
$^1$H NMR (200 MHz, CDCl$_3$): (ppm) 0.92-1.08 (m, 3H), 1.04 (s, 6H), 1.15-1.42 (m, 2H), 1.60-1.87 (m, 3H), 2.23-2.44 (m, 3H). δ (ppm) 16.16, 19.29, 30.43, 35.47, 37.09, 39.04, 46.71, 49.42, 120.36.
MS [e/m (%)]: 151 (M$^+$, 0.2), 136 (25), 119 (13), 111 (29), 109 (10), 108 (20), 96 (27), 95 (100), 94 (11), 84 (16), 83 (69), 82 (31), 81 (11), 69 (52), 68 (10), 67 (20), 56 (24), 55 (29), 53 (11), 41 (34), 39 (17).
IR (film, cm$^{-1}$): 931w, 1064w, 1316w, 1366m, 1379m, 14124, 1463m, 2246m, 2866m, 2930s, 2952s.

EXAMPLE 4

Preparation of
2-(2,4,4-trimethylcyclopentyl)-acrylonitrile (5)

1.1 eq. of sodium borohydride are placed in ethanol at 10° C. under an inert atmosphere. Methyl 2-cyano-2-(2,4,4-trimethylcyclopentylidene)acetate B is added thereto dropwise. The reaction medium is stirred at ambient temperature overnight and is then neutralized with acetone. It is subsequently poured onto a cold 10% HCl solution. The aqueous phase is extracted twice with MTBE. The combined organic phases are washed with a sodium bicarbonate solution and then with an aqueous sodium chloride solution. After drying over magnesium sulfate, filtering through paper and evaporating the solvent, 3-hydroxy-2-(2,4,4-tri-methylcyclopentyl)propanenitrile is obtained in the form of four diastereomers in the proportions of 11:13:23:53.

The 3-hydroxy-2-(2,4,4-trimethylcyclopentyl)propanenitrile is placed in dichloromethane at 10° C. under an inert atmosphere. 2.2 eq. of DBU (diazabicyclo[5.4.0]undec-7-ene) and a few crystals of DMAP (4-dimethylaminopyridine) are added thereto, followed, dropwise, by 1.2 eq. of trifluoroacetic anhydride. The reaction medium is stirred at ambient temperature overnight and is then poured onto water. The aqueous phase is extracted once with dichloromethane. The combined organic phases are washed with water. After drying over magnesium sulfate, filtering through paper and evaporating the solvent, the crude product, obtained in the form of two diastereomers in proportions of 70:30, is distilled under reduced pressure.

B.p.=35° C./0.3 torr
Olfactory description: green, fruity, peach skin, honey.
Major Isomer:
$^1$H NMR (200 MHz, CDCl$_3$): δ (ppm) 0.85 (d, J=7.2 Hz, 3H), 0.96-1.06 (m, 6H), 1.10-1.17 (m, 2H), 1.64-1.83 (m, 4H), 2.17-2.48 (m, 1H), 2.55-2.64 (m, 1H).
$^{13}$C NMR (50 MHz, CDCl$_3$): δ (ppm) 18.94, 31.70, 40.84, 42.07, 46.98, 48.61, 49.20, 50.39, 203.41
MS [e/m (%)]: 163 (M$^+$, 1), 148 (21), 121 (10), 120 (12), 107 (10), 106 (40), 84 (100), 83 (15), 79 (21), 77 (13), 55 (16), 41 (21), 39 (13).
Minor Isomer:
$^1$H NMR (200 MHz, CDCl$_3$): δ (ppm) 0.85 (d, J=7.2 Hz, 3H), 0.96-1.06 (m, 6H), 1.10-1.17 (m, 2H), 1.64-1.83 (m, 4H), 2.17-2.48 (m, 1H), 2.55-2.64 (m, 1H).
$^{13}$C NMR (50 MHz, CDCl$_3$): δ (ppm) 16.94, 30.64, 35.64, 36.46, 46.12, 48.51, 49.67, 50.65, 203.41.
MS [e/m (%)]: 163 (M$^+$, 0.4), 148 (12), 106 (29), 84 (100), 79 (17), 77 (11), 69 (46), 55 (11), 41 (18), 39 (11).
IR (film, cm$^{-1}$): 841w, 932s, 1078w, 1195w, 1294w, 1367m, 1378m, 1407w, 1461m, 1618m, 2222m, 2867m, 2953s.

EXAMPLE 5

Preparation of
2-(2,4,4-trimethylcyclopentyl)-propanenitrile (6)

A solution containing 1 equivalent of 2-(2,4,4-trimethylcyclopentyl)acrylonitrile 5 in toluene and 5% by weight of 5% palladium-on-charcoal is placed in an autoclave, under 20 bar of hydrogen, at 40° C. At the end of the reaction, the autoclave is purged with nitrogen and the solution is filtered through celite. The filtrate is concentrated. The crude product, obtained in the form of four diastereomers in proportions of 8:18:22:52, is purified by distillation.

B.p.=46° C./0.7 torr
Olfactory description: green, rustic, artemisia, woody.
4 Superimposed Isomers:
$^1$H NMR (200 MHz, CDCl$_3$): δ (ppm) 0.91-1.03 (m, 6H), 1.09-1.11 (m, 3H), 1.31-1.92 (m, 2H), 1.25-1.39 (m, 3H), 1.72-1.74 (m, 1H), 2.21-2.43 (m, 1H), 2.59-2.84 (m, 1H).
$^{13}$C NMR (50 MHz, CDCl$_3$ major isomer (52%)): δ (ppm) 16.51, 20.91, 28.73, 30.88, 30.99, 35.95, 38.42, 46.23, 49.64, 50.78, 123.32.
MS [e/m (%)], 52% isomer: 165 (M$^+$, 1), 150 (49), 133 (32), 111 (65), 109 (10), 96 (19), 95 (100), 83 (54), 81 (14), 69 (69), 67 (14), 56 (11), 55 (43), 53 (11), 41 (32), 39 (14).
MS [e/m (%)], 22% isomer: 165 (M$^+$, 0.4), 150 (57), 133 (26), 111 (33), 96 (14), 95 (100), 83 (68), 81 (11), 69 (47), 67 (12), 55 (34), 41 (25), 39 (12).

MS [e/m (%)], 18% isomer: 165 (M⁺, 0.3), 150 (31), 133 (17), 122 (11), 111 (84), 110 (17), 109 (19), 96 (19), 95 (83), 94 (11), 84 (29), 83 (54), 82 (13), 81 (15), 69 (100), 67 (17), 56 (18), 55 (49), 53 (13), 41 (40), 39 (17).

MS [e/m (%)], 8% isomer: 165 (M⁺, 0.1), 150 (29), 133 (19), 111 (87), 110 (16), 109 (18), 96 (15), 95 (83), 94 (14), 84 (32), 83 (56), 82 (13), 81 (17), 69 (100), 67 (15), 56 (15), 55 (49), 53 (11), 41 (38), 39 (16).

IR (film cm⁻¹): 979w, 1103w, 1197w, 1319w, 1366m, 1381m, 1461m, 2238m, 2867m, 2952s.

EXAMPLE 6

Preparation of 2-(2,4,4-trimethylcyclopentyl)-acetaldehyde (7)

2-(2,4,4-Trimethylcyclopentyl)acetonitrile 4 is placed in toluene at 10° C. under an inert atmosphere. 1.2 eq. of Dibal (diisobutylaluminum hydride) are added thereto dropwise. The reaction medium is stirred at ambient temperature for a few hours and then poured onto a 20:40:40 mixture of acetic acid, water and ice. The aqueous phase is extracted once with toluene. The combined organic phases are washed with a sodium bicarbonate solution and then with an aqueous sodium chloride solution. After drying over magnesium sulfate, filtering through paper and evaporating the solvent, the crude product, obtained in the form of two diastereomers in proportions of 70:30, is distilled under reduced pressure.

B.p.=50° C./0.3 torr

Olfactory description: very green, citrus, spicy, cumin, very powerful.

Major Isomer:

¹H NMR (200 MHz, CDCl₃): δ (ppm) 1.05 (2d, J=7.0 Hz and J=6.8 Hz, 6H), 1.57-1.64 (m, 2H), 1.94-1.98 (m, 1H), 2.28-2.34 (m, 1H), 2.52-2.71 (m, 2H), 7.14-7.28 (m, 5H), 9.65 (s, 1H).

¹³C NMR (50 MHz, CDCl₃): δ (ppm) 10.26, 17.71, 33.71, 33.91, 35.43, 51.88, 126.27, 128.71 (2C), 128.81 (2C), 142.49, 205.95.

MS [e/m (%)]: 154 (M⁺, 2), 110 (35), 95 (100), 69 (21), 55 (17), 41 (17).

Minor Isomer:

¹H NMR (200 MHz, CDCl₃): δ (ppm) 0.89 (2d, J=7.0 Hz and J=6.8 Hz, 6H), 1.57-1.64 (m, 2H), 1.94-1.98 (m, 1H), 2.28-2.35 (m, 1H), 2.52-2.71 (m, 2H), 7.14-7.28 (m, 5H), 9.64 (s, 1H).

¹³C NMR (50 MHz, CDCl₃): δ (ppm) 8.57, 15.78, 32.59, 34.02, 36.97, 50.93, 126.27, 128.71 (2C), 128.81 (2C), 142.49, 205.95.

MS [e/m (%)]: 154 (M⁺, 0.5), 110 (36), 109 (13), 95 (100), 83 (11), 69 (33), 55 (21), 41 (22).

IR (film, cm⁻¹): 698s, 747m, 1454m, 1496m, 1603w, 1721s, 2704w, 2860m, 2933m, 2963m, 3026m, 3062w.

EXAMPLE 7

Preparation of 2-(2,4,4-trimethylcyclopentyl)-acrylaldehyde (8)

2-(2,4,4-Trimethylcyclopentyl)acrylonitrile 5 is placed in toluene at 10° C. under an inert atmosphere. 1.2 eq. of Dibal (diisobutylaluminum hydride) are added thereto dropwise. The reaction medium is stirred at ambient temperature for a few hours and is then poured onto a 20:40:40 mixture of acetic acid, water and ice. The aqueous phase is extracted once with toluene. The combined organic phases are washed with a sodium bicarbonate solution and then with an aqueous sodium chloride solution. After drying over magnesium sulfate, filtering through paper and evaporating the solvent, the crude product, obtained in the form of two diastereomers in proportions of 70:30, is distilled under reduced pressure.

B.p.=40° C./0.3 torr

Olfactory description: green, citrus, woody, powerful.

Major Isomer:

¹H NMR (200 MHz, CDCl₃): δ (ppm) 0.88 (d, J=6.4 Hz, 3H), 1.05 (2s 6H), 1.22-1.34 (m, 2H), 1.60-1.87 (m, 2H), 2.04-2.17 (m, 1H), 2.57-2.67 (m, 1H), 6.01 and 6.28 (2s, 2H), 9.56 (s, 1H).

¹³C NMR (50 MHz, CDCl₃): δ (ppm) 18.61, 31.78, 37.28, 39.56, 45.53, 49.06, 50.60, 133.39, 153.26, 195.50.

MS [e/m (%)]: 166 (M⁺, 35), 151 (89), 137 (30), 133 (43), 124 (17), 123 (60), 110 (26), 109 (100), 108 (21), 107 (21), 105 (20), 96 (12), 95 (88), 93 (25), 91 (24), 84 (29), 83 (39), 82 (11), 81 (58), 79 (32), 77 (22), 70 (12), 69 (57), 68 (11), 67 (39), 65 (11), 56 (10), 55 (42) 53 (27), 43 (16), 41 (58) 39 (31).

Minor Isomer:

¹H NMR (200 MHz, CDCl₃): δ (ppm) 0.59 (d, J=7.2 Hz, 3H), 1.05 (2s, 6H), 1.22-1.34 (m, 2H), 1.60-1.87 (m, 2H), 2.04-2.17 (m, 1H), 2.57-2.67 (m, 1H), 6.07 and 6.20 (2s, 2H), 9.56 (s, 1H).

¹³C NMR (50 MHz, CDCl₃): δ (ppm) 18.13, 31.54, 34.56, 37.28, 40.47, 43.24, 49.74, 134.33, 151.82, 195.50.

MS [e/m (%)]: 166 (M⁺, 25), 151 (66), 137 (27), 133 (29), 124 (14), 123 (44), 110 (20), 109 (100), 108 (18), 107 (17), 105 (14), 95 (68), 93 (20), 91 (22), 84 (72), 83 (39), 82 (10), 81 (57), 79 (29), 70 (11), 69 (86), 67 (32), 65 (10), 56 (12), 55 (39), 53 (23), 43 (13), 41 (57), 39 (29).

IR (film, cm⁻¹): 895w, 937m, 1190w, 1242w, 1364w, 1376w, 1459m, 1623w, 1693s, 2696w, 2865m, 2952m.

EXAMPLE 8

Preparation of 2-(2,4,4-trimethylcyclopentyl)-propanal (9)

2-(2,4,4-Trimethylcyclopentyl)propanenitrile 6 is placed in toluene at 10° C. under an inert atmosphere. 1.2 eq. of Dibal (diisobutylaluminum hydride) are added thereto dropwise. The reaction medium is stirred at ambient temperature for a few hours and is then poured onto a 20:40:40 mixture of acetic acid, water and ice. The aqueous phase is extracted once with toluene. The combined organic phases are washed with a sodium bicarbonate solution and then with an aqueous sodium chloride solution. After drying over magnesium sulfate, filtering through paper and evaporating the solvent, the crude product, obtained in the form of three diastereomers observed by GC in proportions of 73:16:11, is distilled under reduced pressure.

B.p.=40° C./0.4 torr

Olfactory description: woody, dry, green, citrus, fresh.

3 Superimposed Isomers:

¹H NMR (200 MHz, CDCl₃): δ (ppm) 0.95-1.03 (superimposed s signals, 6H), 1.07-1.11 (superimposed d signals, 3H), 1.17-1.32 (m, 2H), 1.40-1.50 (m, 1H), 1.62-1.71 (m, 1H), 1.81-2.05 and 2.20-2.23 (2m, 2H), 2.35-2.48 (m, 1H), 9.64 and 9.70 (2s, 1H).

¹³C NMR (50 MHz, CDCl₃): 73% isomer: δ (ppm) 9.43, 19.34, 31.21, 31.40, 37.0, 37.40, 45.90, 47.10, 48.65, 50.46, 205.88.

MS [e/m (%), 73% isomer]: 168 (M⁺, 1), 111 (14), 110 (49), 95 (100), 83 (26), 69 (30), 58 (10), 55 (27), 41 (17).

MS [e/m (%), 16% isomer]: 168 (M⁺, 0.1), 111 (19), 110 (71), 97 (13), 95 (100), 83 (40), 69 (52), 67 (10), 58 (11), 55 (42), 43 (11), 41 (24).

MS [e/m (%), 10% isomer]: 168 (M⁺, 1), 111 (20), 110 (37), 109 (12), 95 (100), 83 (79), 82 (15), 69 (45), 67 (13), 58 (33), 55 (45), 43 (12), 41 (27), 39 (10).

MS [e/m (%)]: 190 (M⁺, 18), 132 (11), 131 (39), 117 (33), 105 (16), 104 (33), 92 (25), 91 (100), 85 (31), 65 (14).

IR (film, cm⁻¹): 840w, 885w, 920w, 971w, 1365w, 1377w, 1460m, 1725s, 2700w, 2866m, 2930m, 2952m.

EXAMPLE 9

Scenting Composition Containing Compound 5

An accord of lemon drop type was prepared from the following ingredients:

| Ingredients | Accord A | Accord B |
| --- | --- | --- |
| Thymol 10% DPG | 5 | 5 |
| Labienoxime 10% DPG | 5 | 5 |
| Citronellyl acetate | 10 | 10 |
| C9 Alcohol | 1 | 1 |
| Hexylcinnamaldehyde | 50 | 50 |
| C8 Aldehyde | 5 | 5 |
| C9 Aldehyde | 2 | 2 |
| β-Pinene | 50 | 50 |
| Citronellol, 98% | 10 | 10 |
| Galaxolide without PE in MIP | 100 | 100 |
| Natural MCP hydrate | 1 | 1 |
| Triplal | 2 | 2 |
| Ethyl maltol | 2 | 2 |
| Vertenex N2 | 30 | 30 |
| Lemon ess Italy SS citropten | 300 | 300 |
| Lemonile | 30 | 30 |
| DPG | 397 | 297 |
| Compound 5 | 0 | 100 |

Evaluation: The addition of compound 5 gives a great deal of power to this lemon note, considerably boosting the "lemon" and "nitrile" notes. The molecule also has an effect with regard to the gourmand angle; the ethyl maltol note is accentuated. The same effect is found in the alcohol and shampoo application.

EXAMPLE 10

Scenting Composition Containing Compound 5

An accord of green peach type was prepared from the following ingredients:

| Ingredients | Accord A | Accord B |
| --- | --- | --- |
| Substance X24242 1% DPG | 20 | 20 |
| Melonal M13303 | 1 | 1 |
| Buchu leaf SS | 1 | 1 |
| Ethyl acetate | 80 | 80 |
| Ethyl acetylacetate | 50 | 50 |
| Phenylethyl alcohol | 50 | 50 |
| Benzaldehyde | 5 | 5 |
| C14 Aldehyde | 40 | 40 |
| C19 Aldehyde | 20 | 20 |
| δ-Dodecalactone | 10 | 10 |
| Damascenone | 1 | 1 |
| δ-Decalactone | 15 | 15 |
| γ-Dodecalactone | 10 | 10 |
| γ-Decalactone | 80 | 80 |
| γ-Valerolactone | 15 | 15 |
| cis-3-Hexenol | 80 | 80 |
| α-Ionone | 4 | 4 |
| cis-Jasmone | 4 | 4 |
| Linalool | 150 | 150 |
| Musc T | 150 | 150 |
| cis-3-Hexenyl salicylate | 80 | 80 |
| Nectaryl | 15 | 15 |

| Ingredients | Accord A | Accord B |
| --- | --- | --- |
| DPG | 109 | 49 |
| Compound 5 | 0 | 60 |

Evaluation: The addition of compound 5 considerably increases the power; it forces the green notes. Several members of a trained panel had the same opinion: they prefer the composition with compound 5. This composition is to be indicated in a shampoo application.

The invention claimed is:

1. A compound of formula (I):

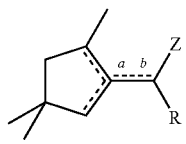

(I)

in which:
R is a hydrogen atom, a $C_1$-$C_6$ alkyl group, a $C_2$-$C_6$ alkenyl group or a =$CH_2$ group;
Z is a CN or CHO group; and
at most one of the bonds represented by dashes is present;
provided that:
if Z is a CHO group and one of the bonds represented by dashes is present, then R is not a hydrogen atom, and
if the bond represented by dashes between the carbons Ca and Cb is present, then R is not a =$CH_2$ group.

2. The compound as claimed in claim 1 having the general formula (I'):

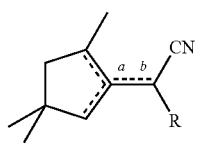

(I')

in which:
R is a hydrogen atom, a $C_1$-$C_6$ alkyl group, a $C_2$-$C_6$ alkenyl group or a =$CH_2$ group; and
at most one of the bonds represented by dashes is present;
provided that:
if the bond represented by dashes between the carbon Ca and Cb is present, then R is not a =$CH_2$ group.

3. The compound as claimed in claim 2, in which R is a hydrogen atom or a methyl or =$CH_2$ group.

4. The compound as claimed in claim 1 having the general formula (I''):

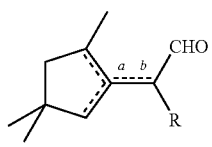

(I'')

in which:
R is a hydrogen atom, a $C_1$-$C_6$ alkyl group, a $C_2$-$C_6$ alkenyl group or a =$CH_2$ group; and
at most one of the bonds represented by dashes is present;
provided that:
if one of the bonds represented by dashes is present, then R is not a hydrogen atom, and
if the bond represented by dashes between the carbon Ca and Cb is present, then R is not a =$CH_2$ group.

5. The compound as claimed in claim 4, in which R is a hydrogen atom or a methyl or =$CH_2$ group.

6. A method of providing a fragrance to a material comprising adding the compound as claimed in claim 1 to said material.

7. A method of masking an odor comprising administering the compound as claimed in claim 1 as a masking agent for an odor.

8. A composition comprising the compound as claimed in claim 1 in combination with at least one other aromatizing or scenting ingredient, and/or at least one solvent, and/or at least one adjuvant.

9. A scenting composition, characterized in that it comprises a compound as claimed in claim 1.

10. A process for the preparation of a compound of formula (I), comprising reacting the compound of formula (A):

(A)

with a diethylphosphonoalkylacetonitrile of formula RCH(CN)PO($OC_2H_5$)$_2$ in which R is a hydrogen atom, a $C_1$-$C_6$ alkyl group or a $C_2$-$C_6$ alkenyl group; or with an alkyl cyanoacetate of formula NCCH$_2$COOR' in which R' is a $C_1$-$C_4$ alkyl group.

\* \* \* \* \*